(12) United States Patent
Cheng et al.

(10) Patent No.: US 7,495,759 B1
(45) Date of Patent: Feb. 24, 2009

(54) DAMAGE AND WEAR DETECTION FOR ROTARY CUTTING BLADES

(75) Inventors: Chi Wah Cheng, Tsing Yi (HK); Lap Kei Eric Chow, Kowloon (HK)

(73) Assignee: ASM Assembly Automation Ltd., Hong Kong (HK)

( * ) Notice: Subject to any disclaimer, the term of this patent is extended or adjusted under 35 U.S.C. 154(b) by 0 days.

(21) Appl. No.: 11/877,099

(22) Filed: Oct. 23, 2007

(51) Int. Cl.
*G01N 21/00* (2006.01)
*B24B 49/00* (2006.01)
(52) U.S. Cl. ......................... 356/237.1; 451/6
(58) Field of Classification Search ........................ None
See application file for complete search history.

(56) References Cited

U.S. PATENT DOCUMENTS 6,552,811 B2 * 4/2003 Hayashi ...................... 356/614

2003/0073382 A1 * 4/2003 Manor ........................... 451/6

FOREIGN PATENT DOCUMENTS

JP 2006-287111 10/2006

* cited by examiner

*Primary Examiner*—Michael P Stafira
(74) *Attorney, Agent, or Firm*—Ostrolenk, Faber, Gerb & Soffen, LLP

(57) ABSTRACT

A method of detecting wear and damage to a rotary cutting blade for singulating a substrate is provided comprising the steps of providing a sensor to locate a first detecting position at an edge of the blade and performing dicing with the blade while the sensor is maintained substantially at the first detecting position for detecting damage to the blade. Subsequently, an extent of wear of the blade is determined by driving the sensor in the direction of the blade to locate a second detecting position at the edge of the blade as a diameter of the blade is reduced due to dicing. Thereafter, while dicing is performed with the blade, the sensor is maintained substantially at the second detecting position for detecting damage to the blade.

14 Claims, 6 Drawing Sheets

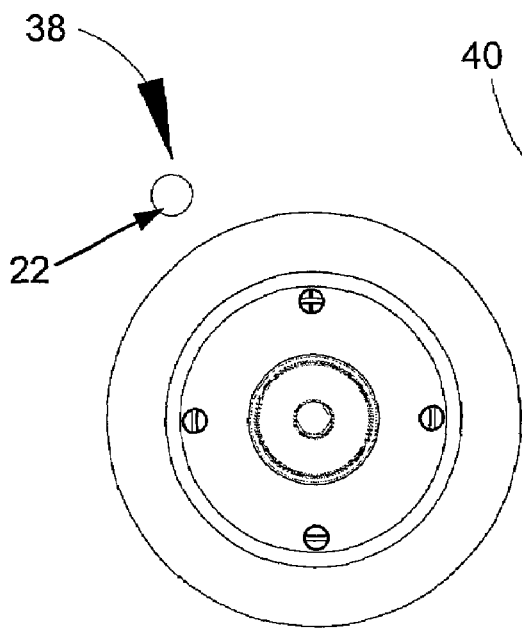
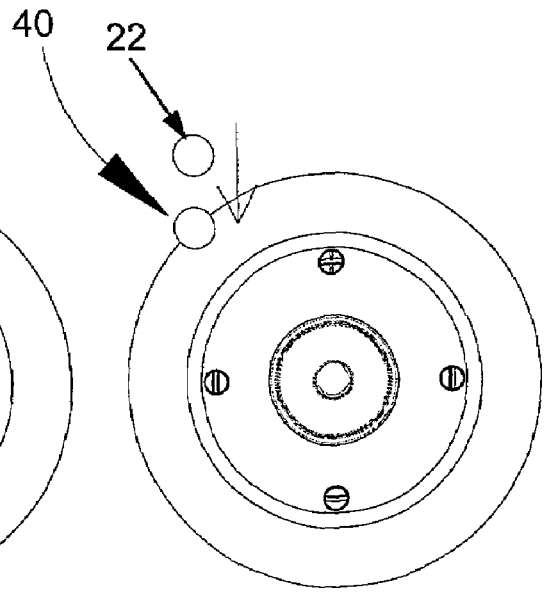
FIG. 5A  FIG. 5B
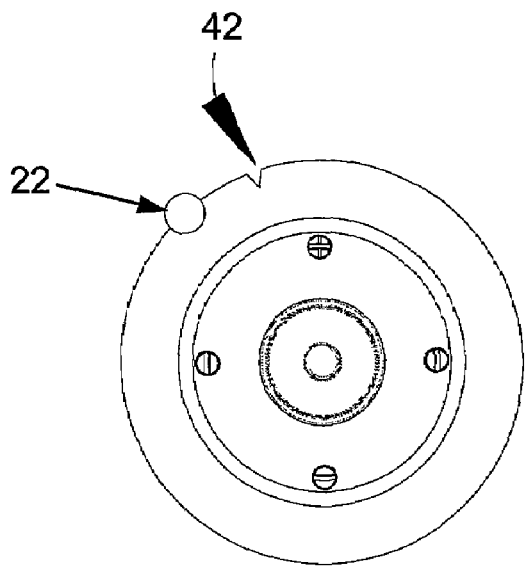
FIG. 6

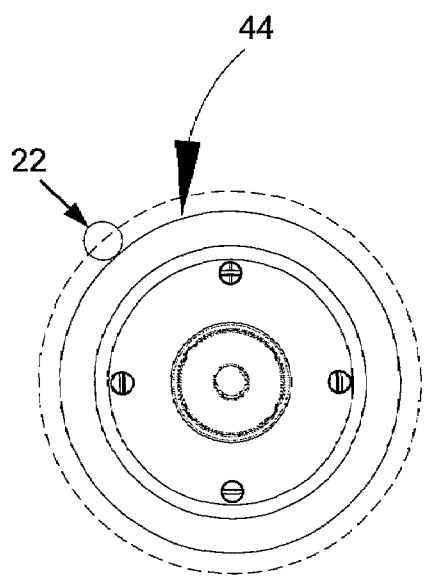
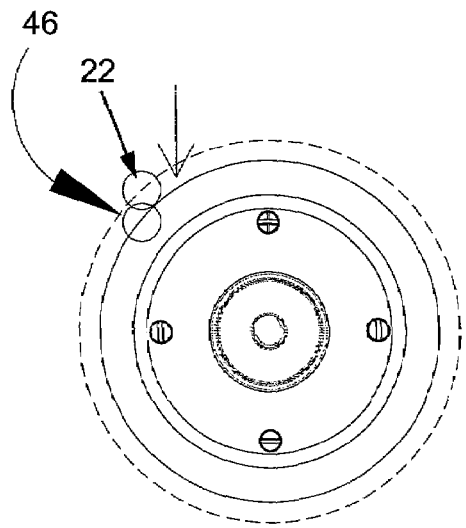
FIG. 7A  FIG. 7B
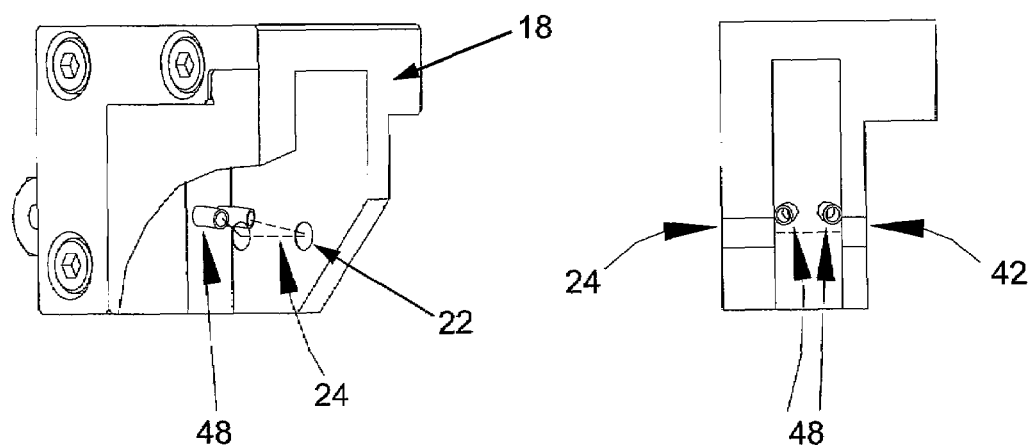
FIG. 8  FIG. 9

DAMAGE AND WEAR DETECTION FOR ROTARY CUTTING BLADES

FIELD OF THE INVENTION

The present invention relates to a singulation system for cutting and separating electronic components, and in particular, to a singulation system comprising a rotary cutting blade.

BACKGROUND AND PRIOR ART

A singulation system for singulation or dicing electronic components, such as semiconductor substrates or packaged semiconductor devices, comprises at least a spindle system and a carrier support such as a chuck table. The axis of the spindle system is orthogonal to the axis of the chuck table and a theta axis table is located on top of the chuck table. The spindle system typically includes either one or two high speed rotary shafts with a cutting blade comprising a circular saw blade each.

Dicing may be performed on the semiconductor substrate in one direction by moving the chuck table under a spindle axis while the saw blade is cutting the semiconductor substrate on a carrier, such as a saw jig, on the theta axis table of the chuck table. The spindle axis may index line by line to complete all the cutting lines required in one direction. Next, the theta table on the chuck table rotates 90 degrees about the theta axis to perform dicing in a direction orthogonal to the first direction. Thus, the semiconductor substrate is singulated into rectangular units.

As singulation is operated by rotating the circular saw blade at high speed, for safety reasons, it is important to monitor and detect the condition of the blade in order to halt the singulation process when the blade is chipped or otherwise damaged. Additionally, the blade will wear out after a period of sawing, resulting in the blade having a reduced diameter. The wearing-out rate of the blade should be monitored regularly in order to accurately adjust the cutting depth of the blade to maintain a constant sawing depth and to replace the blade at an appropriate time.

FIG. 1 is a schematic drawing of a typical through beam sensor 100 located near a saw blade 102 for detecting blade damage. The sensor 100 is placed at a fixed distance from the edge of the blade 102 such that a sensing line 106 monitors the edge of the blade 102 continuously and is able to detect a chipped blade. However, the position of the sensor 100 relative to the edge of the blade must be adjusted manually with a screw 104 when the diameter of the blade 102 decreases as the blade wears off. During adjustment of the sensor 100, the singulation operation must be stopped, which affects productivity. It would be beneficial to be able to monitor damage to the saw blade without interrupting the singulation operation to manually adjust the position of the sensor 100.

Conventionally, optical or contact methods may be used for detecting and measuring the extent of wearing off of a saw blade. These methods are illustrated in FIG. 2. The optical method uses an optical sensor 106 located at a fixed position at some distance from a rotary blade 102. The sensor 106 comprises a light emitting component and a light receiving component positioned opposite each other across a gap which receives the saw blade. Separate water and air nozzles 108 are located within the gap for cleaning the light emitting and receiving components of the optical sensor 106.

After the water nozzles are deactivated, water droplets remaining on the light emitting and receiving components are removed by air jets directed from the air nozzles. Therefore, the light emitting and receiving components are kept clean and dry, that is, they are free from contaminants such as chips and sawing dust from the singulation process. This allows accurate measurement of the extent of wear of the rotary blade. Measurement of wear is conducted by indexing the rotary blade 102 downwards to an optical sensing line in the gap and its index position at the sensor 106 is recorded. When the blade diameter is reduced due to wearing off during singulation, the blade 102 would have to be indexed further downwards to be level with the same optical sensing line. The difference in the index positions is equivalent to the extent of wear of the blade.

In the contact method, the blade 102 is indexed downwards to a standard reference surface 110 located at some distance from the blade 102. When the blade 102 touches the reference surface 110, the index position is recorded. Next, if the blade diameter is reduced as the blade 102 is worn off, the blade 102 will be required to index further to become level with the reference surface 110. The difference in index positions is equivalent to the extent of wear of the blade 102.

Both the contact and optical methods of measuring the extent of wear of the saw blade as described above are slow and inhibit normal machine operation as the saw blade 102 during the singulation operation is far from the optical sensor or the reference surface. It would thus be advantageous to be able to measure an extent of wear of the blade without moving the saw blade 102 over relatively large distances for detecting its edge.

A prior art example of an optical method for damage and wear detection of a saw blade is found in U.S. Pat. No. 6,552,811 entitled "Cutting Blade Detection Mechanism for a Cutting Machine". It discloses a dicing machine comprising a typical through beam sensor similar to that illustrated in FIG. 1 herein for detecting a chipped saw blade. It further discloses an optical sensor comprising light emitting and receiving components as described above for measuring wear value of the saw blade. Contamination of the sensor by the chips and sawing dust during singulation is cleansed by jetting water followed by jetting air at the sensor. Whilst this increases the reliability of readings with regard to the blade, multiple nozzles comprising separate water supply nozzles and air supply nozzles are deployed. This makes the machine complex and increases the number of components required. It is desirable to reduce the number of components for easier machine maintenance and to reduce the need for stocking additional spare parts.

Another prior art example of a singulation system which uses the optical method for detecting the extent of wear is Japanese Patent Publication No. 2006-287111 entitled "Cutting Device and Blade Condition Detecting Method". This prior art discloses a single blade detection sensor for both damage detection and wear detection of a saw blade. The sensor can be indexed by migration means to two different locations for separately carrying out the functions of damage detection and wear detection of the saw blade. Switching means is employed to toggle the sensor between the two locations for carrying out the two detection functions. The toggling between the two detection functions at the two locations is undesirable as this affects the reliability and stability of measuring the blade wear value. Additional time is also required to repeatedly move the sensor between the two locations to perform the two functions. It would be advantageous to eliminate the need for switching between the two detection modes and locations to simplify the measuring algorithm and to achieve increased accuracy and stability.

SUMMARY OF THE INVENTION

It is thus an object of the invention to seek to provide a blade detection system which detects blade damage and wear more efficiently than the aforesaid prior art and which reduces travel time for a sensor while performing damage detection and wear detection.

Accordingly, the invention provides a method of detecting wear and damage to a rotary cutting blade for singulating a substrate, comprising the steps of: providing a sensor; driving the sensor to locate a first detecting position at an edge of the blade; performing dicing with the blade while the sensor is maintained substantially at the first detecting position for detecting damage to the blade during dicing; driving the sensor in the direction of the blade to locate a second detecting position at the edge of the blade as a diameter of the blade is reduced due to dicing for determining an extent of wear of the blade; and thereafter performing dicing with the blade while the sensor is maintained substantially at the second detecting position for detecting damage to the blade during dicing.

It would be convenient hereinafter to describe the invention in greater detail by reference to the accompanying drawings which illustrate one embodiment of the invention. The particularity of the drawings and the related description is not to be understood as superseding the generality of the broad identification of the invention as defined by the claims.

BRIEF DESCRIPTION OF THE DRAWINGS

The present invention will be readily appreciated by reference to the detailed description of a preferred embodiment of the invention when considered with the accompanying drawings, in which:

FIGS. 5A and 5B are side views of a rotary saw blade with a sensor of a sensor head located at a home position away from the blade, and with the sensor located at a blade damage detecting position respectively;

FIG. 6 is the side view of the rotary saw blade which has a chipped surface along the edge of the blade wherein the sensor is located at the blade damage detecting position;

FIGS. 7A and 7B are side views of the rotary saw blade with the sensor located at a first blade edge detecting position and the sensor having searched and relocated to a second blade edge detecting position at the edge of the blade respectively;

FIG. 8 is a partially exposed side view of the sensor housing of the blade detection system showing two fluid/air nozzles within the housing; and FIG. 9 is a front view of the sensor housing of FIG. 8 showing the two fluid/air nozzles.

DETAILED DESCRIPTION OF THE PREFERRED EMBODIMENT OF THE INVENTION

The preferred embodiment of the present invention will be described hereinafter with reference to the accompanying drawings.

Figure 1:
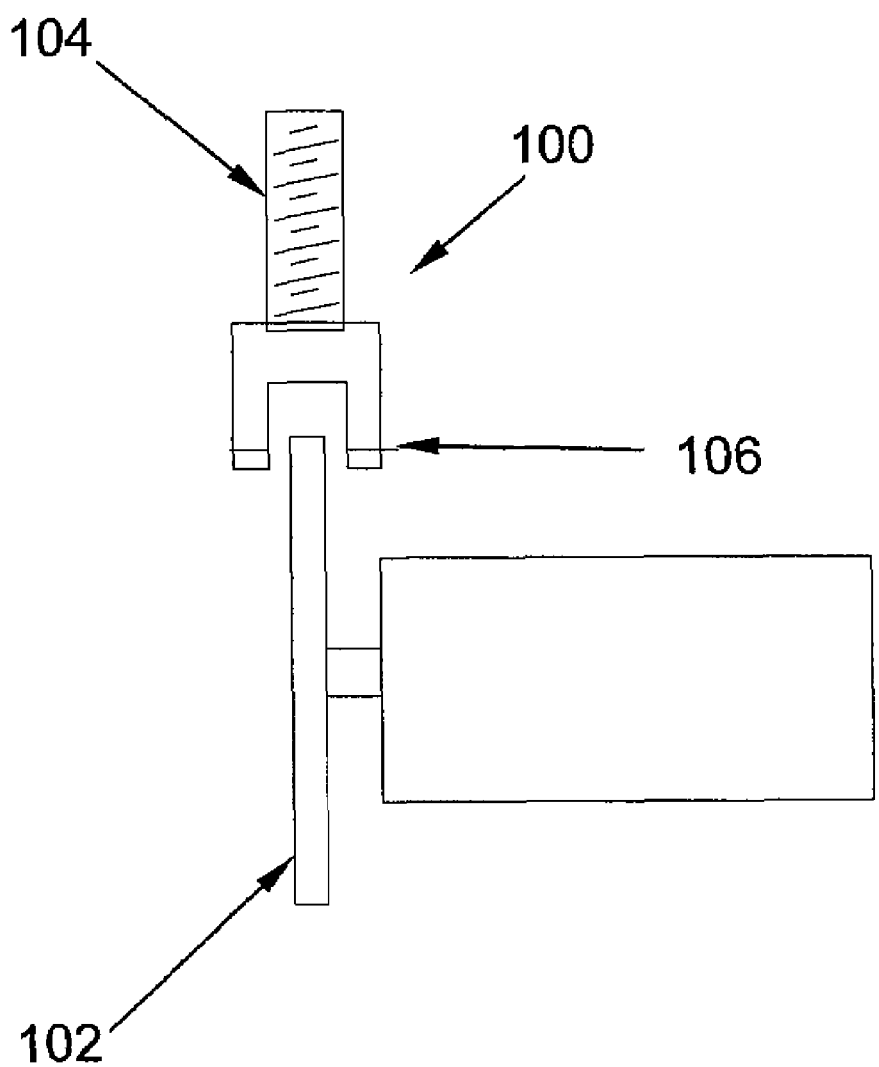
FIG. 1 is a schematic drawing of a typical through beam sensor located adjacent to a saw blade for detecting blade damage.
Figure 2:
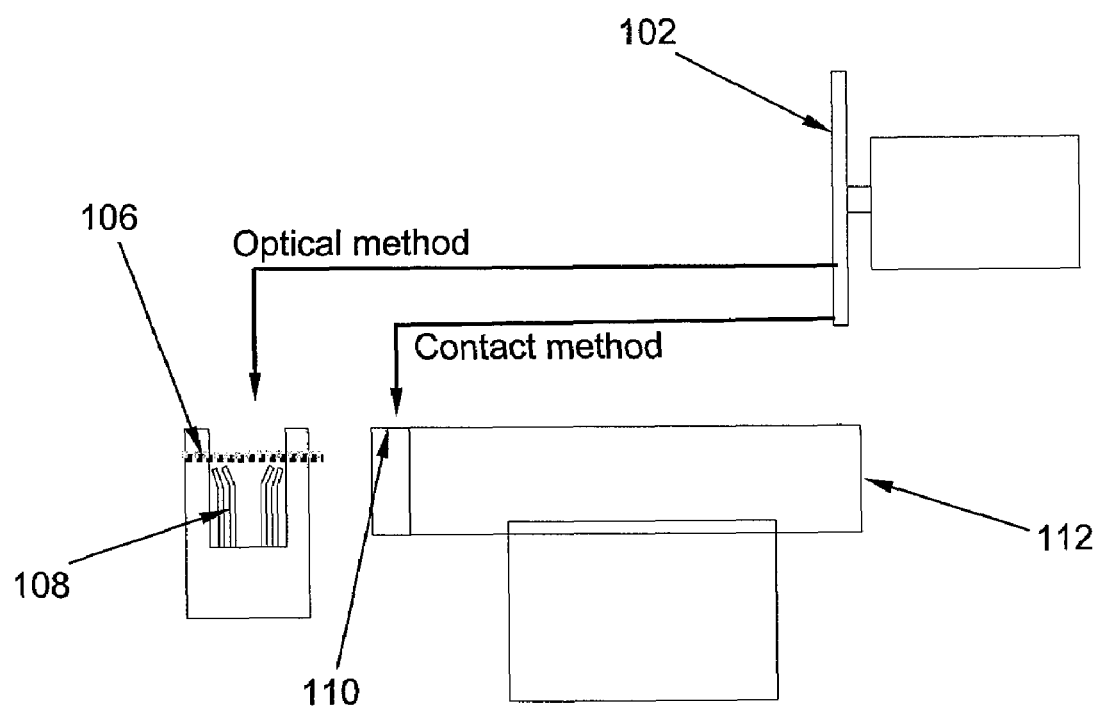
FIG. 2 is a schematic drawing illustrating typical optical and contact methods for detecting and measuring the extent of wearing off of a saw blade.
Figure 3:
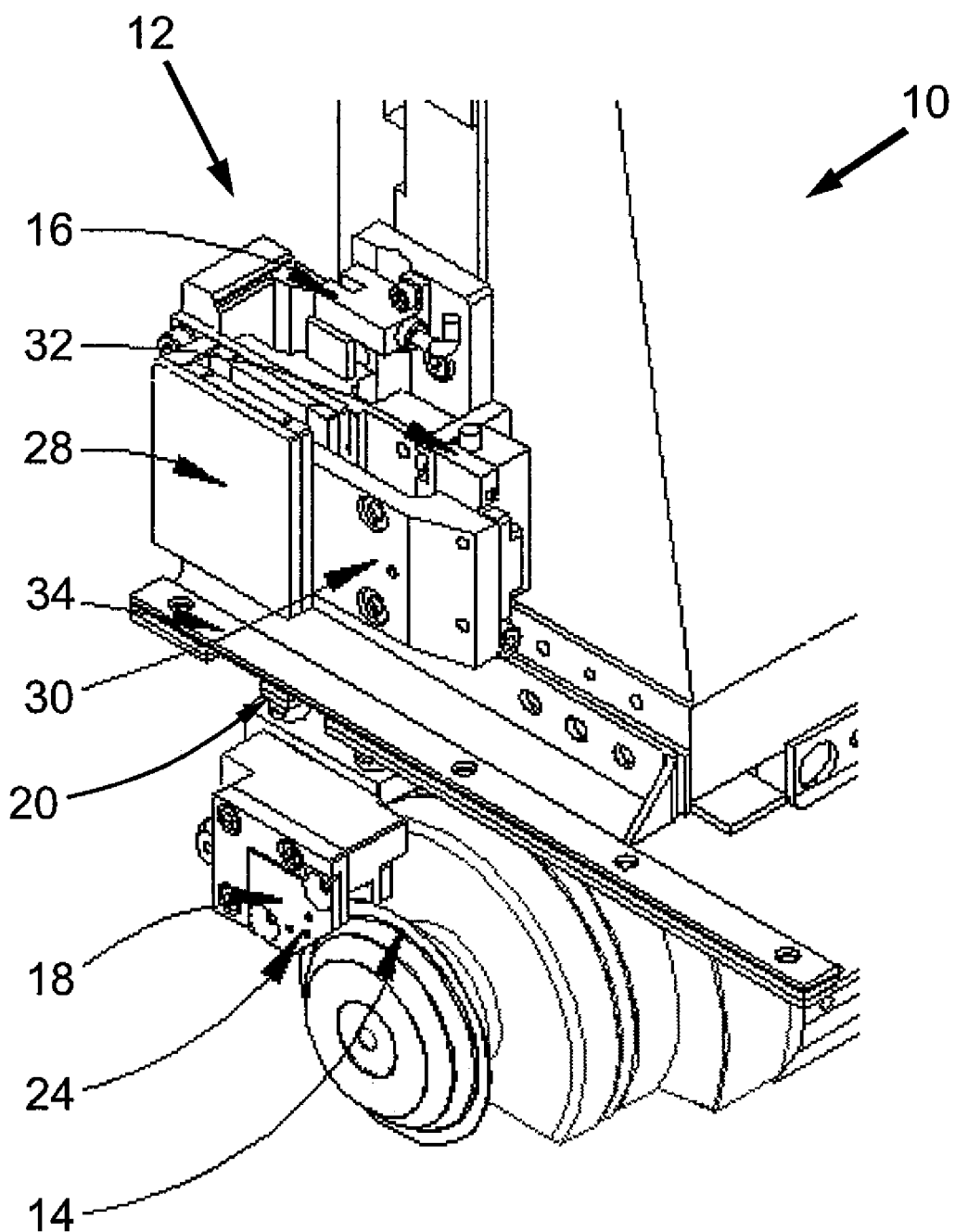
FIG. 3 is an isometric view of a singulation system incorporating a blade detection system according to the preferred embodiment of the invention.

FIG. 3 is an isometric view of a singulation system 10 for singulating substrates incorporating a blade detection system 12 according to the preferred embodiment of the invention. The blade detection system 12 is located immediately above a rotary saw blade 14. This system 12 further comprises a home sensor 16, a sensor housed in a sensor housing 18, cylindrical guide rods 20, movable coils and other connecting parts. A through beam sensor is located within the sensor head 24 and enclosed in the sensor housing 18.

The sensor housing 18 may be driven by a linear direct drive motor mechanism comprising a linear motor 28 and a movable assembly 30 and indexed up and down using the guide rods 20 and a bearing 26. The sensor housing 18 is connected to the direct drive motor mechanism via the cylindrical guide rods 20 so as to drive the sensor housing 18 linearly by driving the guide rods 20. A linear scale head 32 is also provided which provides feedback on the indexing position of the sensor head 24. The home sensor 16 is fixed at the top of the system 12 and the whole movable assembly 30 is indexed with respect to the home sensor 16 during startup of the system. The position of the home sensor 16 is used as a standard reference for indexing. A fluid cover 34 may also be provided for separating and shielding the direct drive motor mechanism from a fluid jet for cleaning the through beam sensor of the sensor head 24.

The sensor head 24 is moved relative to the rotary blade 14 to a blade detecting position by means of the direct drive motor mechanism. Thus, manual adjustment of the sensor head 24 is not necessary. The direct drive motor mechanism automatically drives the guide rods 20 to slide along the bearing 26 so as to guide the sensor head 24 to a position at the edge of the blade as the diameter of the rotary saw blade 14 is reduced during singulation.

Figure 4:
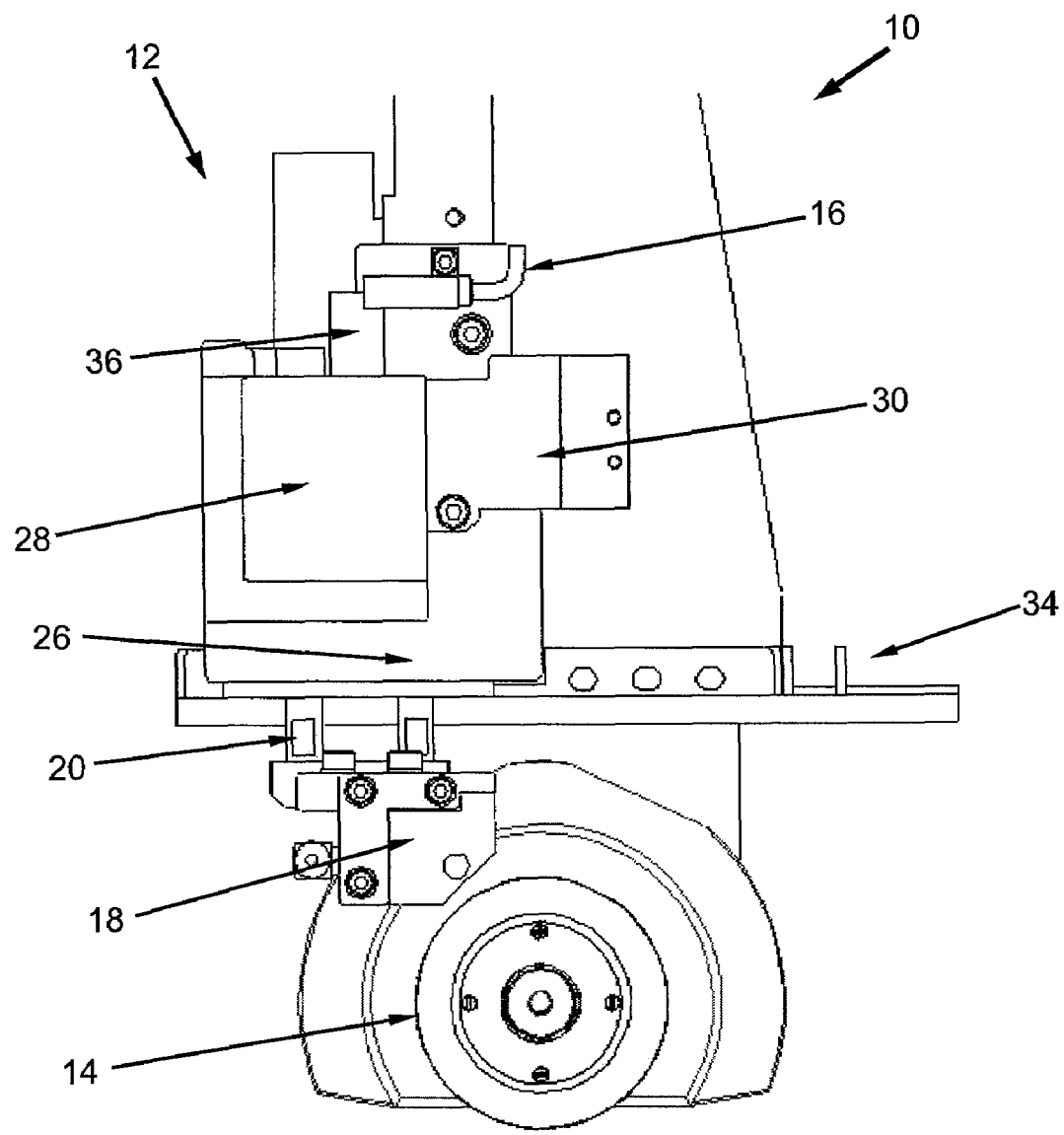
FIG. 4 is a side view of the blade detection system of FIG. 3.

FIG. 4 is a side view of the blade detection system 12 of FIG. 3. The movable assembly 30 is located at a home position such that the sensor flag 36 is aligned with the home sensor 16. At the home position, the sensor head 24 is not at the edge of the rotary saw blade 14 but is located above the rotary saw blade 14.

FIGS. 5A and 5B are side views of a rotary saw blade 14 with a sensor 22 of the sensor head 24 located at the home position 38 away from the blade 14, and with the sensor 22 located at a blade damage detecting position 40 respectively.

In FIG. 5A, the sensor 22 of the sensor head 24 is at the home position 38 and cannot detect the edge of the rotary saw blade 14. In FIG. 5B, the sensor 22 is indexed by driving it towards the edge of the rotary blade 14 to locate a first position at an optimal blade damage detecting position 40 at the edge of the rotary saw blade 14. The sensor 22 preferably comprises a light-emitting element and a light-receiving element, and this position may be determined by a predetermined light receiving level of the light-receiving element of the sensor 22. The sensor 22 is maintained substantially at this first position while the rotary saw blade 14 is dicing the substrate for blade damage detection.

FIG. 6 is the side view of the rotary saw blade 14 which has a chipped surface 42 along the edge of the blade 14 wherein the sensor 22 is located at the blade damage detecting position 40. The sensor 22 monitors the light receiving level of its light-receiving element. When the chipped surface 42 is detected by the sensor 22, the blade detection system 12 will report an error and prompts the halting of the singulation operation in order to change the blade 14.

FIGS. 7A and 7B are side views of the rotary saw blade 14 with the sensor 22 located at a first blade edge detecting position 44, and the sensor 22 having searched and been driven towards the blade 14 to a second position at a second blade edge detecting position 46 at the edge of the blade 14 respectively. In FIG. 7A, a reduction in the diameter of the blade 14 is shown. When the diameter of the blade 14 decreases, the light receiving level of the sensor 22 increases. This prompts the blade detection system 12 to drive the sensor head 24 in the direction of the rotary blade 14 to search for the edge of the rotary blade 14 at which the predetermined light-receiving level is reached.

In FIG. 7B, the side view of the rotary saw blade 14 of FIG. 7A shows the sensor head 24 having searched and relocated to the second blade detecting position 46 on the edge of the blade 14. To arrive at the second blade detecting position 46, the sensor 22 has further searched and indexed in the direction of the rotary saw blade 14 along the initial search direction until the predetermined light receiving level is reached. The wear value of the blade 14 with reduced diameter can therefore be measured by calculating the distance moved by the sensor 22 from the first blade edge detecting position 44 to the second blade edge detecting position 46.

The second blade edge detecting position 46 helps to determine the extent to which the blade diameter has reduced and at the same time helps to locate an optimal position to index the sensor 22 to the blade damage detecting position 40 for carrying out blade damage detection. Thus, the sensor 22 may be maintained substantially at the second blade edge detecting position 46 to perform blade damage detection at this second position for detecting damage to the blade 14 during dicing. Preferably, the second blade edge detecting position 46 is the same as the blade damage detecting position 40, which may both be determined by the same predetermined light-receiving level of the sensor.

The relative position between the sensor 22 and the edge of the blade 14 is maintained by indexing the sensor 22 from time to time towards the inner diameter of the blade as the blade diameter is gradually being reduced by blade wear. As the travel distance of the sensor 22 is short, the indexing operation can be conducted during a relatively short idle time such as during unloading of a singulated substrate and loading of a new substrate for singulation, such that the depth of cut can be easily adjusted from substrate to substrate by locating a new detecting position at the edge of the blade 14 after dicing each substrate. Thus, the singulation operation does not have to be interrupted or stopped during damage and wear detection, and the efficiency of the operation can be improved.

FIG. 8 is a partially exposed side view of the sensor housing 18 of the blade detection system 12 showing two fluid/air nozzles 48 within the sensor housing 18. Each fluid/air nozzle 48 is aimed at a lens of the sensor 22. As there are two such lenses (one for light emitting and one for light receiving), two fluid/air nozzles 48 are required. The fluid/air nozzles 48 deliver jets of cleaning fluid, such as water, followed by jets of air for drying the lens of the sensor 22 for a programmable duration.

The lens of the sensor 22 are kept contamination free from sawing dust and chips during singulation of the semiconductor substrates to prevent inhibition of the light beam emitted and received for detecting blade damage or wear. A valve (not shown) that serves each of the fluid/air nozzles 48 switches the fluid/air nozzles 48 alternately between jetting cleaning fluid and jetting clean compressed air at the lens of the sensor 22. As the cleaning fluid and drying air are emitted from the same channel and are directed at the same spot on the lens of the sensor 22, the lens of the sensor 22 can be dried more directly and effectively. That is, no fluid residue will be left on the lens after cleaning. After a programmable period of cleaning and drying the lens, the fluid/air jets are deactivated. The resulting clean and dry lens allows blade detection to be performed accurately and reliably.

FIG. 9 is a front view of the sensor housing 18 of FIG. 8 showing the two fluid/air nozzles 48. The opening of each nozzle 48 is directed at a lens of the sensor 22 housed in each wall of the sensor housing 18.

It should be appreciated that the singulation system 10 incorporating the blade detection system 12 has the advantage of measuring wear value and detecting blade damage in real time since the blade detection system 12 is located immediately above the rotary blade 14 and adjacent thereto. Furthermore, since only a short time duration is required for indexing the sensor head 24 to the next blade detection location, this can be done during idling time of the singulation operation machine such as loading/unloading substrates for singulation without having to stop the machine. The shorter time needed for wear measurement also allows more frequent measurements to be made. Therefore, the cutting depth of the saw blade into the substrate can be adjusted frequently from substrate to substrate so as to increase the accuracy and efficiency of singulation.

The use of the direct drive motor mechanism means eliminates manual adjustment of the through beam sensor 22. This drives the guide rods 20 to slide smoothly to move the sensor head 24 accurately to an optimal blade damage and/or wear detection position. Accurate and reliable damage detection and wear measurements can be obtained in this way. The use of a pair of cylindrical guide rods connecting the actuator and the sensor head facilitates water-sealing between the sawing process and the upper actuating system.

The preferred embodiment of the present invention not only makes use of a single device, namely the sensor 22, to perform both blade damage detection and wear measurement, the sensor 22 does not have to alternately move between two locations repeatedly or have to switch between two detection modes for separately detecting blade damage and measuring wear value as with the prior art. As there is no back-and-forth movement of the sensor 22 relative to the edge of the blade as with the prior art, the sensitivity level of the sensor 22 can be maintained so that better sensing accuracy can be achieved. Accordingly, the blade detection system 12 is more stable and may be easily maintained as a result. In addition, the sensing cycle time is reduced.

By having a single nozzle for delivering both cleaning fluid and drying compressed air instead of having separate fluid nozzles and air nozzles, the blade detection system 12 helps to eliminate residual fluid droplets around the sensor lens 22. Moreover, as only a single device is deployed to perform both blade damage detection and wear measurement and combined fluid/air nozzles instead of separate fluid and air nozzles are used, easier maintenance of the system is possible and fewer spare parts and smaller space are required.

The invention described herein is susceptible to variations, modifications and/or additions other than those specifically described and it is to be understood that the invention includes all such variations, modifications and/or additions which fall within the spirit and scope of the above description.

The invention claimed is:

1. Method of detecting wear and damage to a rotary cutting blade for singulating a substrate, comprising the steps of:
   providing a sensor;

driving the sensor to locate a first detecting position at an edge of the blade;

performing dicing with the blade while the sensor is maintained substantially at the first detecting position for detecting damage to the blade during dicing;

driving the sensor in the direction of the blade to locate a second detecting position at the edge of the blade as a diameter of the blade is reduced due to dicing for determining an extent of wear of the blade; and thereafter performing dicing with the blade while the sensor is maintained substantially at the second detecting position for detecting damage to the blade during dicing.

2. Method as claimed in claim 1, wherein the sensor has a light-emitting element and a light-receiving element, and the first and second detecting positions are determined by the light-receiving element reaching a predetermined light receiving level at the respective positions.

3. Method as claimed in claim 1, wherein the step of detecting damage to the blade comprises the step of monitoring a light receiving level of the sensor at the first and second positions respectively, which prompts halting of the dicing operation upon detection of blade damage.

4. Method as claimed in claim 1, wherein the step of determining the extent of wear of the blade further comprises the step of calculating the distance the sensor is driven from the first position to the second position.

5. Method as claimed in claim 1, wherein the sensor is driven to locate a new detecting position at the edge of the blade after dicing every substrate.

6. Method as claimed in claim 1, wherein the sensor is driven to locate a new detecting position at the edge of the blade during loading of a new substrate for dicing.

7. Method as claimed in claim 1, wherein the step of moving from the first position to the second position is conducted without having to stop a singulation operation.

8. Method as claimed in claim 1, further comprising the step of providing a linear direct drive motor to drive the sensor.

9. Method as claimed in claim 8, further comprising the step of connecting the sensor to the direct drive motor via cylindrical guide rods so as to drive the sensor linearly by driving the guide rods.

10. Method as claimed in claim 8, further comprising the step of separating the direct drive motor from the sensor with a fluid cover positioned therebetween.

11. Method as claimed in claim 1, further including the step of cleaning the sensor with a nozzle aimed at the sensor, the nozzle being operative to eject both cleaning fluid and drying air at the sensor.

12. Method as claimed in claim 11, wherein the nozzle ejects cleaning fluid following by drying air.

13. Method as claimed in claim 11, wherein the sensor comprises a light-emitting element and a light-receiving element, and the step of cleaning the sensor further comprises aiming first and second nozzles at the light-emitting and light-receiving elements respectively to eject both cleaning fluid and drying air at the elements.

14. Method as claimed in claim 1, wherein the sensor is located above the blade at a home position prior to locating a detecting position.

\* \* \* \* \*